United States Patent [19]

Heinze et al.

[11] Patent Number: 4,823,797

[45] Date of Patent: Apr. 25, 1989

[54] APPARATUS AND METHOD FOR IMPEDANCE MEASUREMENT OF BODY TISSUES

[75] Inventors: Roland Heinze; Karl Stangl, both of Munich, Fed. Rep. of Germany

[73] Assignee: Siemens Aktiengesellschaft, Berlin and Munich, Fed. Rep. of Germany

[21] Appl. No.: 61,547

[22] Filed: Jun. 15, 1987

[30] Foreign Application Priority Data

Jun. 16, 1986 [DE] Fed. Rep. of Germany ....... 3620276

[51] Int. Cl.⁴ .............................................. A61N 1/36
[52] U.S. Cl. .............. 128/419 PG; 128/668; 128/671; 128/734
[58] Field of Search ............. 128/419 P, 419 PG, 734, 128/668, 671

[56] References Cited

U.S. PATENT DOCUMENTS

| | | | |
|---|---|---|---|
| 3,532,086 | 10/1970 | Underwood | 128/2.1 |
| 3,608,542 | 9/1971 | Pacela | 128/2.1 R |
| 3,994,284 | 11/1976 | Voelker | 128/2.05 F |
| 4,580,575 | 4/1986 | Birnbaum et al. | 128/671 |
| 4,686,987 | 8/1987 | Salo et al. | 128/419 PG |
| 4,697,591 | 10/1987 | Lekholm et al. | 128/419 PG |
| 4,738,264 | 4/1988 | Orlando | 128/671 |

FOREIGN PATENT DOCUMENTS 0074126 of 0000 European Pat. Off. .
2070282 of 0000 United Kingdom .

*Primary Examiner*—Leo P. Picard
*Assistant Examiner*—Jessica J. Harrison
*Attorney, Agent, or Firm*—Hill, Van Santen, Steadman & Simpson

[57] ABSTRACT

An apparatus for impedance measurement of body tissue has a signal source which impresses an electrical signal in body tissue, circuitry for acquiring an impedance signal from the body tissue dependent on the impressed electrical signal, and an evaluation stage for evaluating the impedance signal by filtering higher frequency components and low frequency components from the impedance signal which correspond to the conductance of the tissue. A correction stage corrects the high frequency signal components with the low frequency signal components by eliminating the higher frequency signal components of influences due to changes in the tissue conductance. The corrected signal is supplied at an output of the correction stage.

16 Claims, 2 Drawing Sheets

APPARATUS AND METHOD FOR IMPEDANCE MEASUREMENT OF BODY TISSUES

BACKGROUND OF THE INVENTION

1. Related application:

The present application is related to the subject matter of a co-pending application of the same inventors entitled "Apparatus For Impedance Measurement Of Body Tissue" filed simultaneously herewith, Ser. No. 061,549.

2. Field of the Invention

The present invention is directed to devices for making an impedance measurement of body tissues, and in particular to such devices wherein an electrical signal is impressed on the body tissue and an impedance signal is acquired therefrom.

3. Description of the Prior Art

Devices for making an impedance measurement of selected body tissue are known in the art which have a signal source which impresses an electrical signal on the body tissue, means for acquiring an impedance signal from the body tissue dependent on the impressed electrical signal, and means for evaluating the impedance signal. A device which includes an evaluation means which filters out only higher frequency signal components from the impedance signal is described in U.S. Pat. No. 4,303,045. This known device is used in conjunction with frequency-controlled heart pacemakers.

Another apparatus of this type is known from U.S. Pat. No. 3,532,086, wherein an evaluation means filters out both lowfrequency and higher-frequency signal components. This device is used for identifying the degree of blood loss during an operation. The low-frequency component is a measure of the blood volume of the patient.

Heretofore, impedance measurements in body tissue (including blood) served the purpose of identifying mechanical volume changes of the body, for example, the stroke volume of the heart, or the volume changes resulting from thorax movement during respiration. Such changes in impedance are used, for example, to control the frequency of the stimulation pulses of a heart pacemaker. The basis of such impedance measurements is the following known physical relationship:

$$R = \frac{1}{\sigma_R} \cdot K_1,$$

wherein R is the impedance, $\sigma_R$ is the conductance of the tissue ($1/\Omega$-cm), and $K_1 = l/F$ is a value (cm$^{-1}$) proportional to the line distance with l being the effective electrode spacing (cm) and F being the effective line cross-section (cm$^2$) between the electrodes.

Changes in the impedance ($\Delta R$) are a measure of the patient respiration and a measure for the stroke volume of the heart. The measurement of periodic impedance fluctuation essentially covers changes $\Delta l$ from a nominal value for l, or $\Delta F$ from a nominal value for F with respect to the line distance, and thus covers the changes $\Delta K_1$. Changes in the impedance are also dependent on changes of the conductance ($\Delta \sigma_R$) because $$R + \Delta R = \frac{1}{\sigma_R + \Delta \sigma_R} \cdot (K_1 + \Delta K_1)$$

applies in accord with the first-stated relationship. Following therefrom, when filtering out the higher frequency components from the impedance signal, is the relationship:

$$\Delta R \approx \frac{\Delta K_1}{\sigma_R + \Delta \sigma_R},$$

i.e., the impedance changes inversely with respect to the conductance. This causes undesired falsifications of the measured value in conventional impedance measuring devices.

SUMMARY OF THE INVENTION

It is an object of the present invention to provide an apparatus for impedance measurement of body tissue wherein falsification of the measured value on the basis of influences due to changes in tissue conductance are not a factor in the measurement of periodic impedance fluctuations.

The above is achieved in accordance with the principles of the present invention in an impedance measuring apparatus wherein the impedance signal is evaluated by filtering out the low-frequency signal components thereof, which correspond to the tissue conductance, and also filtering out the higher frequency signal components and using the filtered-out low-frequency signal components to correct the higher frequency signal components by eliminating the influence on the higher frequency signal components of changes in the tissue conductance. A corrected signal is thus obtained which can be used, for example, to control the stimulation frequency of a heart pacemaker.

The invention is based in part on the perception that low-frequency signal components of the impedance signal are a measure of the conductance of the tissue on which an electrical signal was impressed, i.e., the low-frequency signal components reflect changes in the conductances. As is known, the higher frequency signal components essentially reflect changes in l and F in the relations identified above. By separating both lower and higher frequency signal components, the higher frequency signal components can be corrected using the low-frequency components, and thus a measured impedance value is obtained which is not influenced by conductance changes, and is thus far more exact than impedance values obtained using conventional devices.

As stated above, the corrected measured impedance value may be supplied to a frequency control unit in a heart pacemaker, for use as a signal for controlling the stimulation frequency, wherein the stimulation frequency is modified given a changing measured value.

DESCRIPTION OF THE PREFERRED EMBODIMENTS

Figure 1:
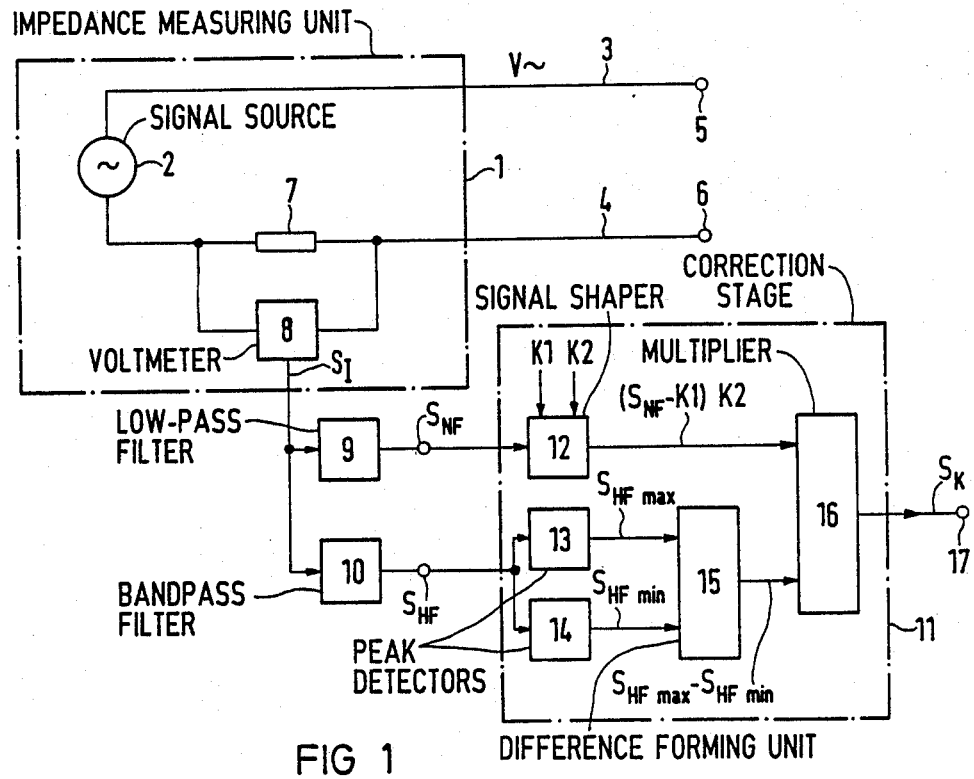
FIG. 1 is a schematic block diagram of an impedance measuring unit and correction stage constructed in accordance with the principles of the present invention.

An impedance measuring unit constructed in accordance with the principles of the present invention is generally shown at 1 in FIG. 1. The impedance measuring unit 1 includes a signal source 2 which may be, for example, a 1 kHz ac voltage generator. The signal source 2 impresses an electrical signal, such as an ac voltage $V\sim$ of unchanging amplitude (for example, a 1 kHz ac voltage) on body tissue (not shown) via electrode lines 3 and 4, and associated electrodes 5 and 6. The apparatus of FIG. 1 is preferably designed for intracorporeal measurement. Thus, at least the electrodes 5 and 6 are implanted in the body tissue, preferably, however, the entire measuring arrangement is implanted. Dependent on the impressed ac voltage $V\sim$, the voltage drop caused by the current in the electrode lines 3 and 4 is measured by a voltmeter 8 through a low-impedance series resistor 7 (for example, 100 ohms).

The output signal of the voltmeter 8 is supplied to an evaluation means which includes a low-pass filter 9 and a bandpass filter 10. The upper limit frequency of the low-pass filter 9 is in the range of from about 0.1 through about 0.4 Hz. The low-pass filter 9 filters only the low-frequency signal components $S_{NF}$, which correspond to the conductance $\sigma_R$ in the body tissue, out of the output signal $S_I$ (impedance signal) of the voltmeter 8.

The bandpass filter 10, which can be adjusted to a frequency range of from about 0.2 through about 0.6 Hz for the acquisition of a respiration signal, or to a frequency range of from about 1 through about 3 Hz for the acquisition of the stroke volume of the heart, passes those higher frequency signal components $S_{HF}$ of the impedance signal within the bandpass range.

The two signal components $S_{NF}$ and $S_{HF}$ are supplied to a correction stage 11, which corrects the higher frequency signal components $S_{HF}$ using the low-frequency signal components $S_{NF}$ to eliminate the influence in the higher frequency signal components of influences due to conductances changes $\Delta\sigma_R$. For this purpose, the correction stage 11 includes a signal shaper 12 which, dependent on entered constants $K_1$ and $K_2$, reshapes the low-frequency signal components $S_{NF}$ into a signal of the form $(K_1/S_{NF})-K_2$. As described in the first-stated relationship, the quantity $K_1$ is based on the geometry of the electrode arrangement 5 and 6 in patients of different sizes, and the quantity $K_2$ accounts for the nature of the transmission path between the electrodes 5 and 6 based on the type of body substance being measured, such as bone tissue or softer tissue.

The correction stage 11 also includes peak detectors 13 and 14 which respectively measure the peaks $S_{HF\,max}$ and $S_{HF\,min}$ of the high-frequency signal components $S_{HF}$. A difference forming unit 15 forms the difference $S_{HF\,max}-S_{HF\,min}$. The signal $S_{HF\,max}-S_{HF\,min}$ is multiplied in a multiplier 16 by the correction signal $(K_1/S_{NF})-K_2$. The result of the multiplication is a corrected signal $S_K$ at a signal output 17 of the correction stage 11.

Figure 2:
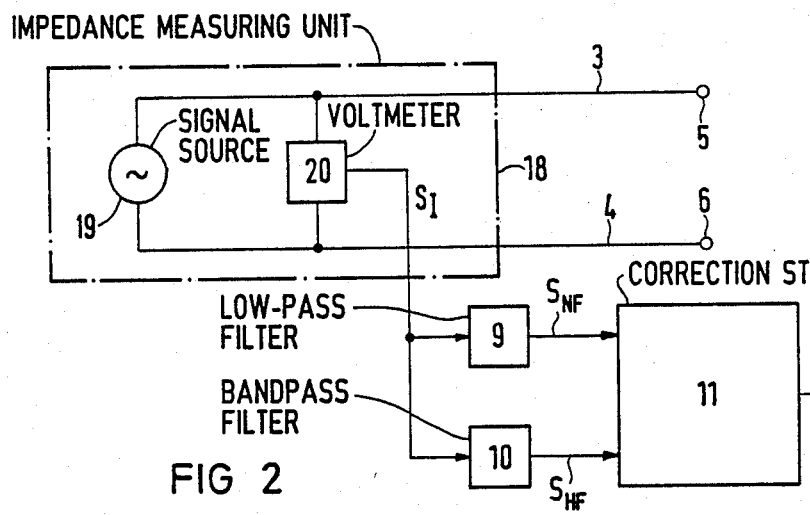
FIG. 2 is a schematic block diagram of a further embodiment of an impedance measuring unit constructed in accordance with the principles of the present invention.

Another embodiment of an impedance measuring unit constructed in accordance with the principles of the present invention is shown in FIG. 2, referenced at 18. In this embodiment, the signal source 19 is an alternating current source (for example, a 1 kHz alternting current source) which impresses an alternating current $I\sim$ (for example, a 1 kHz alternating current) on the body tissue via the electrode lines 3 and 4 and the associated electrodes 5 and 6. Again, the entire measuring arrangement is preferably designed as an intracorporeal measuring system. In this embodiment, the ac voltage between the electrodes 5 and 6 is measured by a parallel voltmeter 20, which contains a divider for forming the value $1/V\sim$. The output signal $S_I$ (impedance signal) of the voltmeter 20 is then evaluated as described above in the filters 9 and 10 and the correction stage 11.

Figure 3:
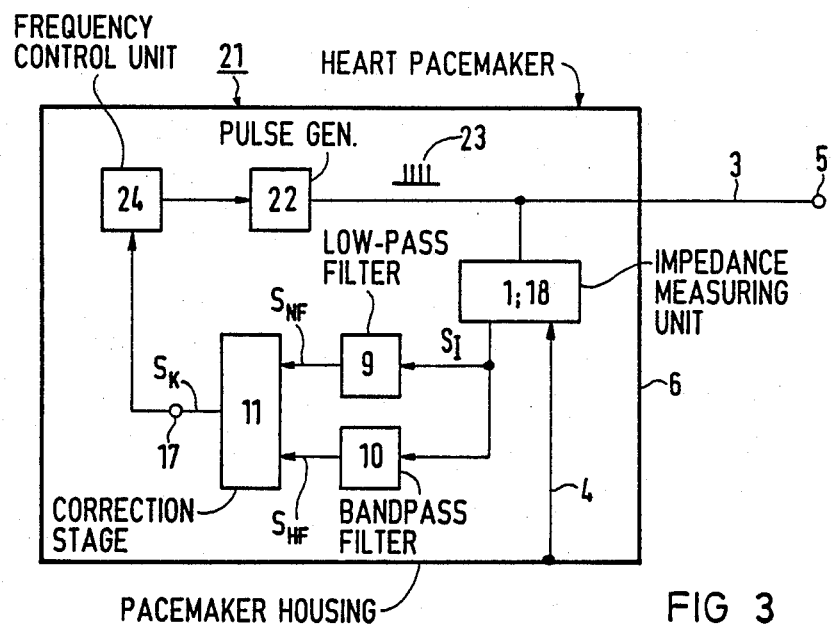
FIG. 3 is a schematic block diagram of a heart pacemaker embodying an impedance measuring unit and correction stage of either FIG. 1 or FIG. 2.

The use of an impedance measuring unit of either the type referenced 1 in FIG. 1 or referenced 18 in FIG. 2, and a correction stage 11, is shown in FIG. 3 in a frequency-controlled heart pacemaker 21. Components already described above are identified in FIG. 3 with identical reference numerals. In the embodiment of FIG. 3, the electrode 5 functions simultaneously as the stimulation electrode for the heart pacemaker 21, whereas the electrode 6 is formed by the conductive (for example, metallic) housing of the heart pacemaker 21. The electrode line 3 corresponds to the stimulation catheter of the heart pacemaker 21.

The heart pacemaker 21 includes a pulse generator 22 which generates stimulation pulses 23. The repetition rate of the stimulate pulses 23 (stimulate frequency) is controllable at the pulse generator 23 by a frequency control unit 24. The stimulation frequency is controlled dependent on the corrected signal $S_K$ obtained from the output 17 of the correction stage 11. Given a changing signal $S_K$, the stimulation frequency is correspondingly modified. The stimulation frequency thus increases when $S_K$ becomes larger, and decreases as $S_K$ becomes smaller.

Although modifications and changes may be suggested by those skilled in the art it is the intention of the inventors to embody within the patent warranted hereon all changes and modifications as reasonably and properly come within the scope of their contribution to the art.

We claim as our invention:

1. An apparatus for impedance measurement of body tissue, said body tissue having a conductance, said apparatus comprising:
    means connected to said body tissue for impressing an electrical signal therein;
    means connected to said body tissue for acquiring an impedance signal therefrom dependent on the impressed electrical signal, said impedance signal including low-frequency components corresponding to said conductance of said body tissue, and higher frequency components;
    means for filtering said low-frequency signal components corresponding to said conductance of said body tissue out of said impedance signal;
    means for filtering said higher frequency signal components out of said impedance signal; and
    means for connecting said higher frequency signal components using said low-frequency signal components for eliminating the influence of changes in said conductance of said body tissue on said higher frequency signal components, and generating a corrected signal at an output.

2. An apparatus as claimed in claim 1, wherein said means for filtering said low-frequency signal components out of said impedance signal is a low-pass filter having an upper limit frequency which permits said low-frequency signal components corresponding to said conductance of said body tissue to pass through said low-pass filter.

3. An apparatus as claimed in claim 2, wherein said upper limit frequency of said low-pass filter is in a range from about 0.1 through about 0.4 Hz.

4. An apparatus as claimed in claim 1, wherein said means for filtering said higher frequency signal components is a bandpass filter.

5. An apparatus as claimed in claim 4, wherein said bandpass filter has a frequency pass band in a range of from about 0.2 through about 0.6 Hz.

6. An apparatus as claimed in claim 4, wherein said bandpass filter has a frequency pass band in a range of from about 1 through about 3 Hz.

7. An apparatus as claimed in claim 1, wherein said means for impressing an electrical signal and said means for acquiring an impedance signal are connected to said body tissue by an electrode arrangement, and wherein said means for correcting includes means for generating a signal of the form $(K_1/S_{NF}) - K_2$, wherein $S_{NF}$ is the low-frequency signal components, $K_1$ is a constant based on the geometry of said electrode arrangement, and $K_2$ is a constant based on the type of body tissue being measured.

8. An apparatus as claimed in claim 7, wherein said correction stage includes:
   means for detecting a maximum peak value $S_{HF\ max}$ of said higher frequency signal components;
   means for detecting a minimum value $S_{HF\ min}$ of said higher frequency signal components;
   means for forming the difference $S_{HF\ max} - S_{HF\ min}$; and
   means for combining said difference with the signal $(K_1/S_{NF}) - K_2$ to generate said corrected signal.

9. An apparatus as claimed in claim 8, wherein said means for combining is a multiplier which multiplies the difference $S_{HF\ max} - S_{HF\ min}$ by the signal $(K_1/S_{NF}) - K_2$.

10. An apparatus as claimed in claim 1, further comprising:
    means for supplying stimulation pulses at a stimulation frequency to the heart of a patient in which said body tissue is disposed; and
    means for controlling the stimulation frequency of said means for supplying said stimulation pulses based on said corrected signal.

11. A method for measuring the impedance of body tissue, said body tissue having a conductance, said method comprising the steps of:
    impressing an electrical signal in said body tissue;
    acquiring an impedance signal from said body tissue dependent on the impressed electrical signal, said impedance signal including low-frequency signal components corresponding to said conductance of said body tissue, and higher frequency signal components;
    filtering said low-frequency signal components corresponding to said conductance of said body tissue out of said impedance signal;
    filtering said higher frequency signal components out of said impedance signal; and
    correcting said higher frequency signal components using said low-frequency signal components to eliminate the influence of changes in said conductance in said body tissue on said higher frequency signal components, and generating a corrected signal.

12. A method as claimed in claim 11, wherein the steps of impressing an electrical signal and acquiring an impedance signal are further defined by impressing an electrical signal and acquiring an impedance signal through an electrode arrangement connected to said body tissue, and wherein the step of correcting is further defined by including the step of:
    generating a signal of the form $(K_1/S_{NF}) - K_2$, wherein $S_{NF}$ is said low-frequency signal components, $K_1$ is a constant based on the geometry of said electrode arrangement, and $K_2$ is a constant based on the type of body tissue being measured.

13. A method as claimed in claim 12, comprising the additional steps of:
    detecting a maximum value $S_{HF\ max}$ of said higher frequency components of said impedance signal;
    detecting a minimum value $S_{HF\ min}$ of said higher frequency components of said impedance signal;
    forming the difference $S_{HF\ max} - S_{HF\ min}$; and combining said difference with the signal of the form $(K_1/S_{NF}) - K_2$ to generate said corrected signal.

14. A method as claimed in claim 13, wherein the step of combining is further defined by multiplying said difference $S_{HF\ max} - S_{HF\ min}$ by the signal $(K_1/S_{NF}) - K_2$.

15. A method as claimed in claim 11, comprising the additional steps of:
    generating stimulation pulses at a stimulation frequency for pacing the heart of a patient in which said body tissue is disposed; and
    controlling the frequency of said stimulation pulses based on said corrected signal.

16. A heart pacemaker for stimulating the heart of a patient in which said pacemaker is implanted, said pacemaker comprising:
    means connected to body tissue having a conductance in said patient for impressing an electrical measurement signal therein;
    means connected to said body tissue for acquiring an impedance signal therefrom dependent on the impressed electrical measurement signal, said impedance signal including low-frequency components corresponding to said conductance of said body tissue, and higher frequency components;
    means for filtering said low-frequency signal components corresponding to said conductance of said body tissue out of said impedance signal;
    means for filtering said higher frequency signal components out of said impedance signal;
    means for correcting said higher frequency signal components using said low-frequency signal components for eliminating the influence of changes in said conductance of said body tissue on said higher frequency signal components, and generating a corrected signal at an output of said means for correcting;
    means for supplying stimulation pulses to said heart of said patient at a variable frequency; and
    control means for varying the frequency of said means for supplying stimulation pulses at least partially in dependence on said corrected signal.

* * * * *